United States Patent [19]
Fogarty et al.

[11] Patent Number: 6,003,906
[45] Date of Patent: Dec. 21, 1999

[54] CONNECTOR FOR ELASTOMERIC CONDUIT

[75] Inventors: Terence M. Fogarty, 1830 River Ridge Rd., Hudson, Wis. 54016; Robert A. Arp, Eden Prairie, Minn.

[73] Assignee: Terence M. Fogarty, Hudson, Wis.

[21] Appl. No.: 08/963,947

[22] Filed: Nov. 4, 1997

[51] Int. Cl.⁶ ........................... F16L 13/14
[52] U.S. Cl. ........................... 285/242; 285/255
[58] Field of Search ................... 288/242, 255, 288/259, 382.2, 421

[56] References Cited

U.S. PATENT DOCUMENTS

| | | | |
|---|---|---|---|
| 3,885,819 | 5/1975 | Egerer et al. | 285/255 |
| 4,537,183 | 8/1985 | Fogarty | 128/79 |
| 4,569,675 | 2/1986 | Prosi | 604/175 |
| 4,632,435 | 12/1986 | Polyaki | 285/243 |
| 4,673,394 | 6/1987 | Fenton et al. | 604/175 |
| 4,704,103 | 11/1987 | Stober et al. | 604/93 |
| 4,772,270 | 9/1988 | Wiita et al. | 604/175 |
| 4,890,866 | 1/1990 | Arp | 285/243 |
| 4,929,236 | 5/1990 | Sampson | 605/175 |
| 4,946,200 | 8/1990 | Blenkush et al. | 285/255 |
| 5,026,344 | 6/1991 | Dijkstra et al. | 604/93 |
| 5,041,098 | 8/1991 | Loiterman et al. | 604/175 |
| 5,045,060 | 9/1991 | Melsky et al. | 604/93 |
| 5,284,368 | 2/1994 | Oetiker et al. | 285/255 |
| 5,360,407 | 11/1994 | Leonard et al. | 604/175 |
| 5,387,192 | 2/1995 | Glantz et al. | 604/93 |
| 5,470,113 | 11/1995 | Schwalm et al. | 285/255 |

FOREIGN PATENT DOCUMENTS

| | | | |
|---|---|---|---|
| 259048 | 11/1963 | Australia | 285/255 |
| 1802610 | 6/1970 | Germany | 285/255 |
| 2716290 | 10/1978 | Germany | 285/255 |
| 2826817 | 1/1980 | Germany | 285/255 |
| 251600 | 11/1987 | Germany | 285/255 |

*Primary Examiner*—Eric K. Nicholson
*Attorney, Agent, or Firm*—Faegre & Benson LLP

[57] ABSTRACT

A connector device for elastomeric conduits includes a connector having a mechanism to allow attachment to a device to be connected to the conduit. The connector includes a frusto-conical barb leading to a shoulder separated by a necked in region. A mating annular clamp includes an inner bore having surfaces that mate with the shoulder and an inwardly projecting annular ring that traps a conduit between the clamp and the neck and barb of the connector. The connector may be mirrored with a like connector to provide a mechanism to attach two conduits rather than a device.

15 Claims, 3 Drawing Sheets

CONNECTOR FOR ELASTOMERIC CONDUIT

BACKGROUND OF THE INVENTION

1. Field of the Invention

This invention relates to connectors used to join elastomeric conduits to devices or another elastomeric conduit.

2. Description of the Related Art

The prior art includes connector devices where a conduit is secured to a connector by:

Clamping the conduit to the connector using a clamp or band that can be constricted by the user, for example, an automotive heater or radiator hose connection. These clamps may be of a screw type where a screw cooperates with a perforated metal band or of a crimped band type (Melsky & Prosi, U.S. Pat. No. 5,045,060, Column 7, line 53) where the band is gathered in tension and crimped to retain the conduit on the connector.

Similarly, elastomeric conduits may be secured to a connector using a restrictive type band such as an electrical strap that is drawn around the conduit in a constrictive manner to retain the conduit on the connector.

Historically, physicians have sutured elastomeric conduits onto connectors as surgical implants. Industrial and medical applications involve clamping or crimping hose fittings by deforming metal or plastic retainers after the connector has been inserted into the conduit.

Medical applications, including surgically implanted conduits, typical involve a connector that is placed in the conduit bore with a clamp that retains the conduit on the connector. In all cases known to the inventors the clamps have:

segments that flex radially outward from the connector, and then return to engage the connector or conduit to secure the conduit to the connector (Fogarty, U.S. Pat. No. 4,537,183), or segments that can be collapsed radially inward to engage the conduit or connector to retain the conduit on the connector, the means of collapsing the segments radially inward being another component of the connector device or an integral part of the connector, clamp or device the connector is being secured to (Arp, U.S. Pat. No. 4,890,866; Sampson, U.S. Pat. No. 4,929,236).

Medical applications, including surgically implanted conduits, that involve placing a connector inside the bore of a conduit and an elastomeric sleeve component over the conduit at the connector. The sleeve may be extended beyond the connector to further act as a strain relief element for the conduit.

A suture may be used to secure the sleeve onto the conduit. The sleeve radially supports the conduit and also prevents the suture from damaging the conduit. Typically the suture would be placed beyond a barb or radial projection on the connector to secure the conduit on the connector.

The sleeve may also be expanded radially to allow installation and then released to constrict the conduit at the connector. The sleeve may also be dilated to increase it's size to allow installation over the conduit, then the dilating media is evaporated causing the sleeve to constrict on the conduit. For example, Freon or isopropyl alcohol will dilate a silicone elastomer conduit (Wiita, et al., U.S. Pat. No. 4,772,270, Column 8, line 64; and 11, Column 7, line 62.) A sleeve may be fabricated from a heat shrink tubing that can be placed over the conduit and then radially shrunk to constrict the conduit (Melsky & Prosi, U.S. Pat. No. 5,045,060, Column 7, line 60.) Medical applications, including surgically implantable conduits, where the connector moves radially inward to allow the clamp and conduit to bypass a barb or radial projection on the connector (Leonard & Wadsworth, U.S. Pat. No. 5,360,407; Dijkstra & Boersma, U.S. Pat. No. 5,026,344). Medical applications where the conduit, sleeve or clamp is secured with an adhesive (Wiita, et al., U.S. Pat. No. 4,772,270).

Industrial and medical applications where the clamp has a twist lock to secure the connection (Loiterman, et al., U.S. Pat. No. 5,041,098; Fenton & Young, U.S. Pat. No. 4,673,394; Glantz, et al., U.S. Pat. No. 5,387,192).

Industrial and medical applications where a feral or sleeve is compressed by another connector component, or where a sleeve has projections that are collapse onto the conduit or connector by another component to secure the connection (Dijkstra & Boersma, U.S. Pat. No. 5,026,344). Industrial and medical applications where the clamp or retaining sleeve is threaded to a connector component or to a device, thus securing the conduit to the connector, or the conduit and connector to the device (Stober & Brencher, U.S. Pat. No. 4,704,103; Prosi, U.S. Pat. No. 4,569,675). Industrial and medical applications where the conduit is solvent or adhesively bonded to the connector, which may engage and share an interface with the conduit bore or conduit outer surface.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

SUMMARY OF THE INVENTION

The connector device described in this invention disclosure may be used to join elastomeric conduits in general use or in special applications such as implantable medical devices. The connector device may be used to join two elastomeric conduits of the same or different dimensions, materials or Durometer (hardness). This is accomplished by configuring each of the opposing connector ends and respective clamps for the intended application. The connector device described in this invention disclosure may be used to join an elastomeric conduit to a device component by providing a suitable means of attachment as described in this disclosure.

The advance over the prior art include:

Simplicity of design

Ease of connector component fabrication

Ease of assembly by end user

This design is simplistic in that the connector device does not require any elements that move radially to allow the conduit to be installed on the connector, or that move radially to secure the conduit to the connector. Furthermore, there are no connector elements that engage clamp elements that move radially to either allow assembly of the connector device or to secure the conduit to the connector device.

This connector may be screw-machined from rod stock or molded. The mold may have a basic design with split cavity halves and a core member(s). The clamp may be screw-machined from rod stock or molded using a lost core method. The ease of fabrication results in a low component cost. If the components are molded the tooling cost is lower than the tooling cost of components with radially movable elements.

This connector device is easy to assemble by the end user, because there are only two components. The user slides the clamp onto the conduit, installs the conduit onto the connector ramp and pushes the clamp onto the connector until it seats against the radial projection on the connector. The connection may be made wet or dry.

This connector device does not require:

an installation tool to advance the clamp onto the connector, or an installation tool to crimp a retaining band, or an installation tool to inwardly collapse gripping elements, or a suture or band to secure the conduit on the connector, or a heat source to shrink a sleeve around the conduit, or a solvent to dilate a sleeve around the conduit at the connector, or an expander tool to radially enlarge a sleeve or clamp to install it, or an installation tool to engage the connector, clamp and conduit, or an adhesive.

BRIEF DESCRIPTION OF THE DRAWINGS

A detailed description of the invention is hereafter described with specific reference being made to the drawings in which.

DESCRIPTION OF THE PREFERRED EMBODIMENTS

Figure 1:
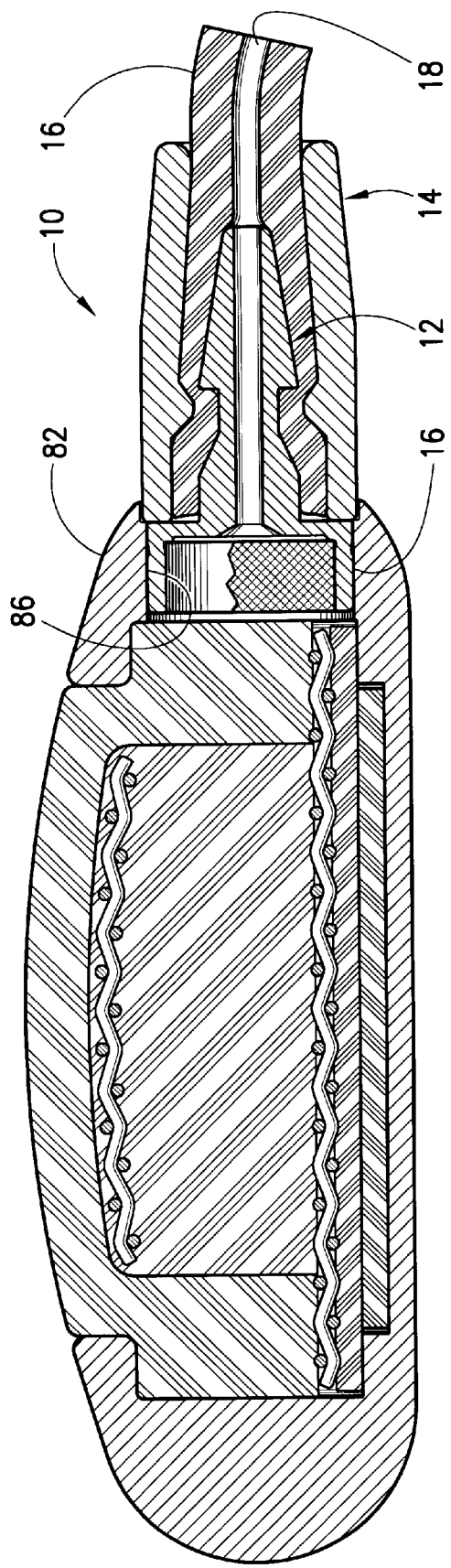
FIG. 1 is a cross-sectional view of an injection port connected to a flexible conduit with a connector device of the invention.

The connector 12 has a frusto-conical shaped barb 20 that engages the bore 18 of the elastomeric conduit 16. The frusto-conical segment 20 has a distal radius 24 at it's minor diameter to ease installation of the conduit 16, to prevent damaging the conduit 16 during installation onto the connector 12, and to improve conduit fatigue resistance where it departs from the connector 12.

The major diameter of the frusto-conical barb 20 also has a proximal radius 26 to prevent 1) damage that might occur to the conduit bore 18 as the conduit 16 bypasses the major diameter of the frusto-conical segment 20 of the connector 12, when the conduit 16 and annular clamp 14 are advanced onto the connector 12 during assembly of the connector device 10, or 2) damage to the conduit bore 18 that may occur after it is secured to the connector device 10, when the conduit 16 is compressed between the clamp 14 and connector 12.

The frusto-conical surface 30 on the connector barb 20 serves as a ramp to expand the conduit 16 and predisposes the conduit bore 18 in the connector device pinch point.

Immediately adjacent the frusto-conical barb 20 is a neck section 28 with a diameter smaller than the major diameter of the frusto-conical segment. The purpose of the neck section 28 is to provide an area where the conduit 16 can be compressed or pinched between the proximal radius 26 located at the major diameter of the frusto-conical segment 20 on the connector 12 and the cooperating annular frusto-conical surface 66 on the annular connector clamp 14.

Beyond the neck area 28 is shoulder 32 that cooperates with the conduit 16 to axially stabilize the annular connector clamp 14. A frusto-conical transition zone 34 connects the neck 28 and shoulder 32. This frusto-conical transition zone 34 provides a ramp for the conduit 16 to advance onto the shoulder segment 32 during installation of the conduit 16 onto the connector 12. Immediately adjacent the shoulder 32 is a radial projection 36 to stop the conduit 16 and annular connector clamp 14. The connector 12 has an annular passage 22 for the transmission of fluid or gas.

The annular connector clamp 14 exterior is configured with a cylindrical surface 50 and a frusto-conical surface 52. The exterior configuration is based on aesthetics and ease of assembly. The frusto-conical section 52 provides a surface to apply lateral force when advancing the clamp 14 onto the connector 12. Because the clamp's annular surfaces are not axially symmetrical, it is important that the user install the clamp 14 in the correct direction. The frusto-conical surface 52 suggests to the user the correct orientation for assembly. The cylindrical surface 50 provides appropriate material thickness and was chosen by the inventors for aesthetic appeal and as a surface that could be easily marked for informational or instructional purposes.

The inner annular surfaces of the clamp 14 cooperate with the exterior surfaces of the connector 12 to secure the conduit 16 on the connector 12 and the clamp 14 on the conduit 16. The clamp annular surfaces consist of three frusto-conical segments and three cylindrical segments. All of these surfaces are in contact with the conduit 16 when the connector device 10 is assembled.

The first cylindrical annular clamp surface 60 corresponds to the shoulder 32 of the connector 12.

The first frusto-conical annular clamp surface 62 corresponds to the frusto-conical transition ramp 34 between the connector shoulder 32 and neck 28.

The second cylindrical annular clamp surface 64 corresponds to the connector neck 28.

The second frusto-conical annular clamp surface 66 corresponds to the radius 26 at the major diameter of the frusto-conical surface 30 on the connector barb 20.

The third frusto-conical annular clamp surface 68 corresponds to the frusto-conical surface 30 on the connector barb 20.

The third cylindrical annular surface 70 extends beyond the connector 12.

The first cylindrical annular clamp surface 60 of the clamp 14 captures the conduit 16 and is stabilized by the conduit 16 and connector neck 28, so that it is less prone to axial instability with the connector 12. The connector device 10 pinch point is defined as the cross-sectional area between the radius 26 on the major diameter of the frusto-conical surface 30 of the connector barb 20 and the second frusto-conical annular surface 66 of the clamp 14. This pinch point is of inconsequential length in relation to the overall length of the clamp 14. Without the stability afforded by the connector shoulder 32, conduit 16 and first cylindrical annular surface 60 of the clamp 14, this pinch point would act as a pivot point and might fatigue the conduit 16 or allow the conduit 16 to escape the pinch point when the conduit is exposed to internal pressurization and axial tension, or even worse tension in an off axis direction. By stabilizing the clamp 14 at the connector shoulder 32, the pinch point also because a source of stabilization. The combined stabilization afforded at the connector shoulder 32 and connector device pinch point are substantial in view of their combined length and distance between them with respect to the overall length of the clamp 14.

The first frusto-conical annular clamp surface 62 further captures the conduit 16 between the opposed frusto-conical transition ramp 34 of the connector 12.

The second cylindrical annular clamp surface 64 causes the conduit 16 to conform around the radius 26 at the major diameter of the frusto-conical surface 30 on the connector barb 20. A cylindrical surface is preferred to a radius or sharp intersection of the first and second frusto-conical annular surfaces. If the clamp 14 is machined, it would be difficult to machine and inspect the confluence of the first and second frusto-conical annular surfaces, to assure that there were no sharp edges that could damage the elastomeric conduit. The cylindrical surface may be more easily radiused where it joins the first and second frusto-conical annular surfaces of the clamp.

The third frusto-conical annular clamp surface 68 cooperates with the frusto-conical surface 30 of the connector barb 20 to capture the conduit 16.

The third cylindrical annular clamp surface 70 acts as a rigid strain relief to prevent flexing of the conduit 16 where the conduit departs from the connector 12. Any flexing of the conduit 16 will occur beyond the connector 12 and will not involve abrasion of the conduit 16 against the connector 12.

The clamp 14 has radii on the exterior and interior surface at both ends. The external radii 78, 80 at ends of the clamp are both aesthetic and to remove sharp edges that would be undesirable to the user. The internal proximal radius 76 at the end of the first cylindrical annular clamp surface 60 is to prevent damage to the exterior surface of the conduit during installation of the clamp 14. The internal radius 74 at the end of the third cylindrical annular clamp surface 70 diminishes the abrasive action on, or cutting of the exterior surface of the conduit 16 as it exits the clamp 14, as a result of tensioning or flexing of the conduit 16.

The connector device 10 is assembled with the conduit 16 by:

1. Sliding the clamp 14 onto the conduit 16, frusto-conical exterior surface 52 first.
2. The conduit 16 is then advanced onto the frusto-conical ramp 30 of the connector barb 20, until the end of the conduit 16 is flush with the end of the largest end of the ramp.
3. The clamp 14 is then advanced toward the connector 12 until it engages the conduit 16 over the connector ramp 30.
4. The clamp 14 is further advanced causing the conduit 16 to advance with it, until they both abut the radial projection 36 on the connector 12. The connection can be made with the connector device components and conduit either wet or dry.

The connector device 10 secures the conduit 16 by capturing the conduit along most of it's length and on either side of a pinch point. The pinch point is stabilized to prevent the escape of the conduit 16 when it is internally pressurized, tensioned or in a worst case, simultaneously subjected to internal pressurization and tensioning.

The connector 12 and clamp 14 may be fabricated from metals or plastic and they do not need to be the same material. For example, the connector 12 could be metal and the clamp 14 plastic or the materials could be reversed. The connector 12 may be screw-machined or molded in either metal or plastic. The clamp 14 may be screw-machined or molded in either metal or plastic using a lost core method.

Preferred Embodiment

The preferred embodiment is depicted in the drawings and represents the initial utilization of the invention. This first application involves connecting an elastomeric conduit in the form of an implantable infusion catheter to an implantable injection port 82 for the delivery of vaso-dilator drugs to the penis for the treatment of incontinence in the men and are shown in FIGS. 1–4.

The connector 12 and clamp 14 are screw-machined from a titanium rod. Titanium was chosen because it is light weight and because the connector 12 was adapted and assembled to an injection port housing fabricated from titanium. It is important to maintain the same nobility of metals in the same corrosive environment, to prevent anodic and cathodic activity between the metals.

The connector 12 and clamp 14 dimensions were developed to optimally function with a conduit (catheter) 16 fabricated from an 80 Shore A Durometer silicone elastomer having a bore 18 of 0.020 inch and an external diameter of 0.081 inch. The connector bore 22 is 0.020 inch and is sized to match the conduit 16 so it does not restrict the flow. The connector 12 is adapted with a collapsible flange segment 84 for press fitting the connector 12 into the aperture 86 in the injection port housing.

Figure 2:
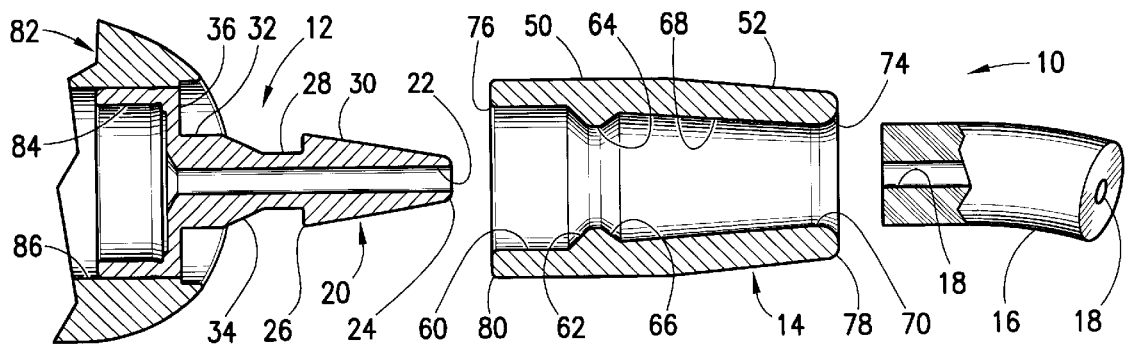
FIG. 2 is a cross-sectional view of the connector device of the invention showing the connector, clamp and conduit prior to assembly.
Figure 3:
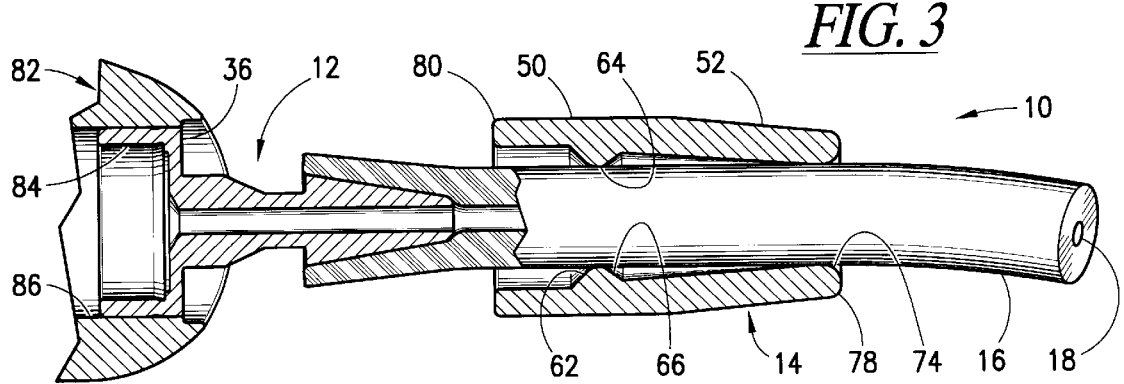
FIG. 3 is a cross-sectional view of the connector device of the invention showing the connector, clamp and conduit during assembly.
Figure 4:
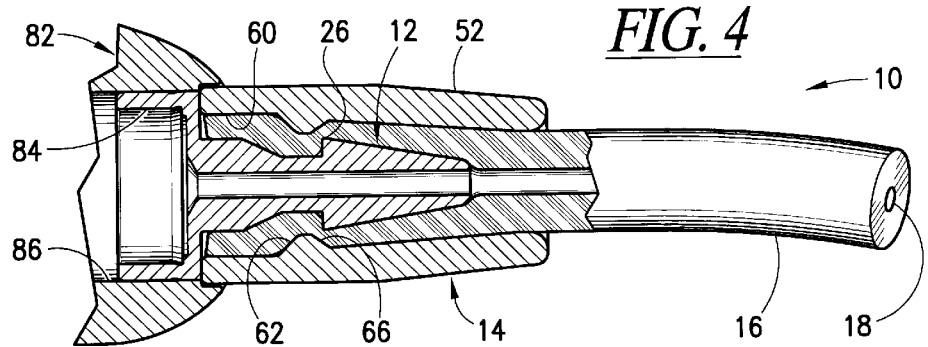
FIG. 4 is a cross-sectional view of the connector device of the invention showing the connector, clamp and conduit after assembly.

FIGS. 2–4 show the assembly of the connector device 10 to a conduit 16. The connector 12 is shown attached to an injection port 82 via a collapsible flange segment 84 in the injection port housing aperture 86. Obviously, the connector may include any type of end fitting as required to make an attachment to whatever device is to be connected.

Figure 5:
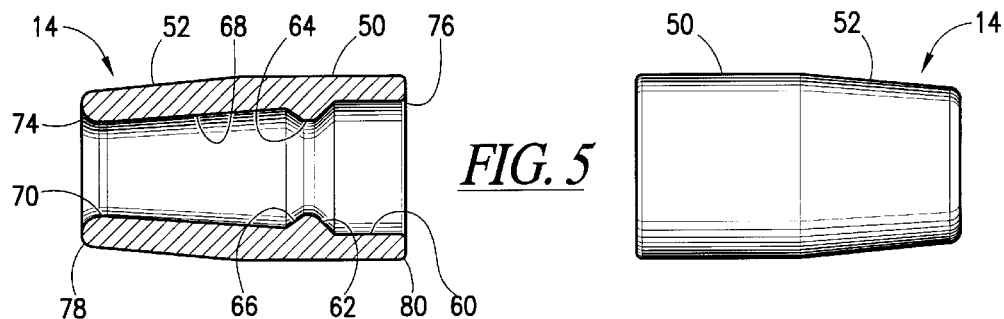
FIG. 5 is a side view and a cross-sectional view of a pair of clamps used to connect two conduits together.
Figure 6:
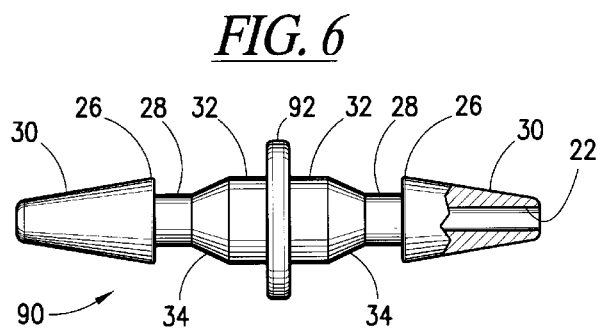
FIG. 6 is a side view partially broken away of a connector for two conduits.
Figure 7:
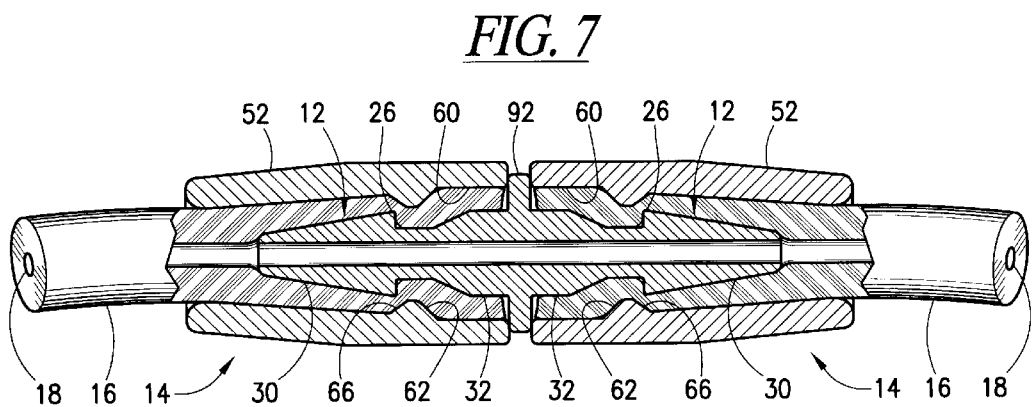
FIG. 7 is a cross-sectional view of an assembled connector device of the invention coupling two conduits together.

FIGS. 5–7 show an alternative embodiment of the invention in which the connector device 10 is used to connect two conduits, rather than a conduit to a device. In such a device, two clamps 14 are utilized and the connector simply needs to be formed in tandem, opposing elements with a single radial projection therebetween. Like element numerals are used on connector 90 to show the similarity of elements. Connector 90 includes a single radial projection 92 in its center. As can be seen, the connector 90 functions in exactly the same manner as connector 12 but is duplicated to connect two conduits.

The apparent simplicity of the connector device tends to obscure the functionality of the invention. The connector and clamp are both fabricated from rigid materials. No deformation of the connector or clamp components or any elements of these components is anticipated or required for the connector device to function. To the contrary, component deformation would compromise the function of the invention. Furthermore, there are no elements of the connector components that move radially to facilitate assembly or secure the conduit in the connector device.

The connector is designed and sized to function with an elastomeric conduit. The invention relies on the deformable characteristics of the elastomeric conduit, both during connector assembly and during its subsequent residence in the connector device. During connector assembly, the clamp is placed on the conduit and the conduit is then installed onto the connector barb, so that the end of the conduit coincides with the largest end of the connector barb.

When the clamp is advanced toward the connector, the clamp first frusto-conical surface, then the clamp second cylindrical annular surface, and finally the clamp second frusto-conical annular surface deform the conduit between the opposing connector second frusto-conical surface of the connector barb. The compression of the conduit continues as the clamp and the conduit advance onto the connector barb. The clamp first frusto-conical annular surface and second cylindrical annular surface combine to engage the conduit so that it advances up the connector barb surface as the clamp is advanced onto the connector. The length of the shoulder, neck and transition area between them are sized to accommodate the length of the conduit that is advanced ahead of the clamp. The end of the conduit abuts the connector radial projection before the end of the clamp does. Therefore, an area is provided between the clamp and connector in the area between the shoulder and barb for the excess conduit to reside in a longitudinally compressed state. This describes how the elastomeric properties of the conduit allow the connector device to be assembled.

Once the connector assembly is accomplished, the conduit compressed between the shoulder and barb exerts a force on the clamp first frusto-conical annular surface and the connector frusto-conical transition between the shoulder and neck in the direction that would cause the clamp and connector to separate. This force causes the clamp to exert compression of the conduit at the pinch point.

The elastomeric conduit is retained in the connector device by the pinch point between the clamp second frusto-conical annular surface and the connector radius at the end of the major diameter of the frusto-conical barb. The clamp first and second annular frusto-conical surfaces and the clamp second annular frusto-conical surface cooperate with the connector neck and frusto-conical transition surface to predispose the conduit in the pinch point. External forces acting on the clamp that might cause the clamp to leave the connector intensify the compression of the conduit resulting in increased resistance to the separation of the clamp from the connector. The conduit, between the connector shoulder and clamp first cylindrical annular surface, axially stabilizes the clamp on the connector against internal forces that might otherwise shift the connector at the pinch point. Instability at the pinch point could progressively allow release of radial segments of the conduit through the pinch point, that might ultimately progress to release of the conduit from the connector device. Therefore, the features of the invention cooperate to prevent such instability and failures.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A connector device for elastomeric conduit comprising:
   a) a connector having a distal and a proximal end and at least one lumen therethrough, said proximal end being constructed and arranged for connection to a device to be connected to a conduit, said connector having a frusto-conical barb extending from said distal end toward said proximal end such that the diameter of said barb is greater proximally than distally, said connector further including a neck section proximal to said barb having a reduced diameter, said connector including a shoulder proximal to said neck section, said shoulder having a diameter greater than said neck section; and
   b) a clamp member having interior walls defining a bore through which a conduit may be inserted, said interior walls including a first cylindrical annular clamp surface which is sized to pass over said connector barb and to be positioned over said shoulder of said connector to clamp a section of an elastomeric conduit to the shoulder, said interior walls further defining an inwardly projecting annular clamp surface sized to be able to pass over said connector barb and to be positioned over the neck section of the connector to clamp a section of an elastomeric conduit to the neck section.

2. The connector device of claim 1 wherein said connector includes a radial projection proximal to said shoulder to limit movement of a conduit proximally over said connector.

3. The connector device of claim 1 wherein said connector includes a frusto-conical transition segment connecting said shoulder and said neck section.

4. The connector device of claim 1 wherein the inwardly projecting clamp surface of said clamp member is formed by a pair of opposing frusto-conical surfaces that meet at a second cylindrical annular clamp surface.

5. The connector device of claim 1 wherein the frusto-conical barb of said connector includes a formed radius adjacent said neck portion.

6. The connector device of claim 1 wherein said connector and clamp members are fabricated from rigid material.

7. The connector device of claim 3 wherein said shoulder, neck and transition segment are constructed and arranged such that a conduit placed between said connector and clamp is in compression between the connector shoulder and barb.

8. The connector device of claim 1 wherein said clamp extends past said connector distal end when assembled over a conduit to thereby improve fatigue resistance of the conduit distal to said connector.

9. The connector device of claim 1 wherein said clamp includes first annular frusto-conical and second annular cylindrical surfaces that deform an elastomeric conduit positioned between said clamp and connector at the frusto-conical surface of said connector barb during assembly.

10. The connector device of claim 1 wherein said clamp is transparent to facilitate inspection of the relationship of the clamp to an underlying conduit.

11. A connector device for coupling two elastomeric conduits comprising:
   a) a connector having a distal and a proximal end and at least one lumen therethrough, said connector having a first frusto-conical barb extending from said distal end toward a central annular radial projection end such that the diameter of said first barb is greater proximally than distally, said connector further including a first neck section proximal to said first barb having a reduced diameter, said connector including a first shoulder proximal to said first neck section, said first shoulder having a diameter greater than said first neck section, said connector having a second frusto-conical barb extending from said proximal end toward a central annular radial projection end such that the diameter of said second barb is greater distally than proximally, said connector further including a second neck section distal to said second barb having a reduced diameter, said connector including a second shoulder distal to said second neck section, said second shoulder having a diameter greater than said second neck section; and b) a pair of clamp members, each clamp member having interior walls defining a bore through which a conduit may be inserted, said interior walls including a first cylindrical annular clamp surface which is sized to pass over said connector barb and to be positioned over said shoulder of said connector to clamp a section of an elastomeric conduit to the shoulder, said interior walls further defining an inwardly projecting annular clamp surface sized to be able to pass over said connector barb and to be positioned over the neck section of the connector to clamp a section of an elastomeric conduit to the neck section.

12. The connector device of claim 11 wherein said connector includes a frusto-conical transition segment connecting each said shoulder to each said neck section.

13. The connector device of claim 11 wherein the inwardly projecting clamp surface of each said clamp member is formed by a pair of opposing frusto-conical surfaces that meet at a second cylindrical annular clamp surface.

14. The connector device of claim 11 wherein each frusto-conical barb of said connector includes a formed radius adjacent said neck portion.

15. A connector device for elastomeric conduit comprising:

a) a connector having a distal and a proximal end and at least one lumen therethrough, said proximal end being constructed and arranged for connection to a device to be connected to a conduit, said connector having a frusto-conical barb extending from said distal end toward said proximal end such that the diameter of said barb is greater proximally than distally, said proximal end of said barb having a radius, said connector further including a neck section proximal to said barb having a reduced diameter, said connector including a shoulder proximal to said neck section, said shoulder having a diameter greater than said neck section, said connector further including a frusto-conical transition segment connecting said shoulder and said neck section; and b) a clamp member having interior walls defining a bore through which a conduit may be inserted, said interior walls including a first cylindrical annular clamp surface which is sized to pass over said connector barb and to be positioned over said shoulder of said connector to clamp a section of an elastomeric conduit to the shoulder, said interior walls further defining an inwardly projecting annular clamp surface formed by a pair of opposing frusto-conical surfaces and sized to be able to pass over said connector barb and to be positioned over the neck section of the connector to clamp a section of an elastomeric conduit to the neck section and form a pinch point between the connector barb radius and one of the frusto-conical surfaces of the inwardly projecting annular clamp surfaces.

* * * * *